(12) United States Patent
Maslana et al.

(10) Patent No.: US 9,283,557 B2
(45) Date of Patent: *Mar. 15, 2016

(54) LAB MEMBERS AND LIQUID HANDLING SYSTEMS AND METHODS INCLUDING SAME

(71) Applicant: PerkinElmer Health Sciences, Inc., Waltham, MA (US)

(72) Inventors: Eugene S. Maslana, Morton Grove, IL (US); Karen A. McElroy, Joliet, IL (US); Dennis F. Malkowski, Yorkville, IL (US); James W. Sim, Evergreen Park, IL (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/718,417

(22) Filed: May 21, 2015

(65) Prior Publication Data
US 2015/0251173 A1    Sep. 10, 2015

Related U.S. Application Data

(63) Continuation of application No. 13/827,411, filed on Mar. 14, 2013.

(60) Provisional application No. 61/617,883, filed on Mar. 30, 2012.

(51) Int. Cl.
*B01L 3/02* (2006.01)
*B01L 9/00* (2006.01)
(Continued)

(52) U.S. Cl.
CPC . *B01L 3/021* (2013.01); *B01L 9/54* (2013.01); *G01N 35/0099* (2013.01);
(Continued)

(58) Field of Classification Search
CPC .. B01L 3/021; G01N 35/0099; G01N 35/109; G01N 35/1067; G01N 2035/1069

USPC .......................................................... 422/509
See application file for complete search history.

(56) References Cited

U.S. PATENT DOCUMENTS

| | | | |
|---|---|---|---|
| 3,444,742 A | 5/1969 | Ellis et al. | |
| 3,657,694 A | 4/1972 | Lindsey | |

(Continued)

FOREIGN PATENT DOCUMENTS

| | | |
|---|---|---|
| EP | 0 571 100 A1 | 11/1993 |
| EP | 1 443 330 A1 | 8/2004 |

(Continued)

OTHER PUBLICATIONS

"Hamilton Robotics: Labware Manipulation Tools," Hamilton Robotics, Retrieved Date: May 3, 2012, From URL: http://www.hamiltonrobotics.com/hamilton-robotics/liquidhandling/star/labware-manipulation-tools/ (3 pages).

(Continued)

*Primary Examiner* — Jill Warden
*Assistant Examiner* — Brittany Fisher
(74) *Attorney, Agent, or Firm* — Myers Bigel & Sibley, P.A.

(57) ABSTRACT

A laboratory liquid handling system includes a pipetting module, a lab member, and a drive system. The pipetting module includes a pipettor including a pipettor shaft and a pipetting tip extending from an end of the pipettor shaft. The lab member includes a body and at least one adapter structure including an interlock feature configured to laterally receive and interlock with the pipettor shaft to releasably secure the lab member to the pipettor shaft. The drive system is operable to: selectively move the pipettor shaft laterally relative to the interlock structure to engage the pipettor shaft with the interlock structure to secure the lab member to the pipetting module; move the pipetting module to transport the lab member secured thereto; and selectively move the pipettor shaft laterally relative to the interlock structure to disengage the pipettor shaft from the interlock structure to thereby release the lab member.

9 Claims, 13 Drawing Sheets

(51) Int. Cl.
*G01N 35/00* (2006.01)
*G01N 35/10* (2006.01)

(52) U.S. Cl.
CPC ......... *G01N 35/1009* (2013.01); *G01N 35/109* (2013.01); *G01N 35/1067* (2013.01); *G01N 2035/1051* (2013.01); *G01N 2035/1069* (2013.01)

(56) References Cited

U.S. PATENT DOCUMENTS

| | | | |
|---|---|---|---|
| 3,855,868 A | | 12/1974 | Sudvaniemi |
| 4,389,374 A | | 6/1983 | Sutton et al. |
| 4,830,832 A | * | 5/1989 | Arpagaus et al. ............... 422/65 |
| 5,365,783 A | | 11/1994 | Zweifel |
| 5,487,997 A | | 1/1996 | Stolp |
| 5,496,473 A | | 3/1996 | Chow |
| 5,525,302 A | | 6/1996 | Astle |
| 5,961,927 A | | 10/1999 | Isaacs |
| 6,156,275 A | | 12/2000 | Dumitrescu et al. |
| 6,203,760 B1 | | 3/2001 | van der Plaats et al. |
| 6,253,807 B1 | * | 7/2001 | Jones ........................... 141/321 |
| 6,417,007 B1 | | 7/2002 | Gittleman et al. |
| 7,018,587 B2 | | 3/2006 | Heath et al. |
| 7,169,361 B2 | | 1/2007 | Arnold et al. .................. 422/526 |
| 7,191,647 B2 | | 3/2007 | Harazin et al. |
| 7,314,598 B2 | | 1/2008 | Nishino |
| 7,411,508 B2 | | 8/2008 | Harazin et al. |
| 7,513,857 B2 | | 4/2009 | Gueller et al. |
| 7,635,326 B2 | | 12/2009 | Gueller et al. |
| 7,858,041 B2 | | 12/2010 | Muraishi et al. .............. 422/511 |
| 8,021,611 B2 | | 9/2011 | Roach et al. |
| 8,057,756 B2 | | 11/2011 | Londo et al. |
| 8,192,698 B2 | | 6/2012 | Londo et al. .................. 422/501 |
| 8,377,396 B2 | | 2/2013 | Meinicke |
| 2001/0028863 A1 | | 10/2001 | Kitagawa ...................... 422/100 |
| 2002/0095998 A1 | | 7/2002 | Kris et al. |
| 2003/0017084 A1 | | 1/2003 | Dale et al. |
| 2003/0215365 A1 | | 11/2003 | Sevigny et al. |
| 2004/0069076 A1 | | 4/2004 | Gamble |
| 2004/0070225 A1 | * | 4/2004 | Meinicke et al. ............. 294/86.4 |
| 2007/0269853 A1 | | 11/2007 | Galiano ........................ 435/39 |
| 2010/0226828 A1 | | 9/2010 | Itoh |
| 2010/0313688 A1 | | 12/2010 | Hiltbrand .................... 73/864.91 |
| 2012/0291872 A1 | | 11/2012 | Brady et al. |

FOREIGN PATENT DOCUMENTS

| | | |
|---|---|---|
| GB | 2 431 600 A | 5/2007 |
| KR | 790001034 B1 | 8/1979 |
| WO | WO 00/08472 A2 | 2/2000 |
| WO | WO 00/25922 A2 | 5/2000 |
| WO | WO 2005/059567 A1 | 6/2005 |
| WO | WO 2006/083695 A2 | 8/2006 |

OTHER PUBLICATIONS

"Hamilton Robotics: Microplate Gripping CO-RE Grip," Hamilton Robotics, Retrieved Date: May 3, 2012, From URL: http://www.hamiltonrobotics.com/hamilton-robotics/liquidhandling/star/labware-manipulation-tools/microplate-co-re-grip/ (2 pages).
"Hamilton Robotics: eSWAP Gripper," Hamilton Robotics, Retrieved Date: May 3, 2012, From URL: http://www.hamiltonrobotics.com/hamilton-robotics/liquidhandling/star/labware-manipulation-tools/swap-external-gripper/ (4 pages).
"Hamilton Robotics: iSWAP Microplate Gripper," Hamilton Robotics, Retrieved Date: May 3, 2012, From URL: http://www.hamiltonrobotics.com/hamilton-robotics/liquidhandling/star/labware-manipulation-tools/iswap-microplate-gripper/ (3 pages).
"Janus® Automated Workstation from PerkinElmer—USA," PerkinElmer, Inc., Retrieved Date: Feb. 9, 2011, From URL: http:las.perkinelmer.com/Catalog/CategoryPage.htm?CategoryID=JANUS (2 pages).
Flaherty, N. (Apr. 23, 2009). JANUS Product Portfolio. PerkinElmer (26 pages).
"Plate-GripX" Xiral, Retrieved Date: Feb. 9, 2011, From URL: http://www.xiril.com/xiril/printable/products/optionsaccessories/plategripx/index.html (1 page).
"SPE Module—automated vacuum extraction" Xiral, Retrieved Date: May 3, 2012, From URL: http://www.xiril.com/xiril/printable/products/optionsaccessories/spemodule/index.html (1 page).
"VERSA Liquid Handling Systems Accessories & Modules" Aurora Biomed, Retrieved Date: Feb. 21, 2011, From URL: http://aurorabiomed.com/liquid-handling-accessories.htm (3 pages).
"Waters: Lid Assembly [M880877BC1]," Waters, Retrieved Date: Apr. 8, 2011, From URL: http://waters.com/waters/partDetail.htm?locale=en_US&partNumber=M880877BC1 (1 page).
International Search Report and Written Opinion issued in corresponding PCT Application No. PCT/US2013/034146, mailed Jul. 25, 2013 (11 pages).

* cited by examiner

LAB MEMBERS AND LIQUID HANDLING SYSTEMS AND METHODS INCLUDING SAME

RELATED APPLICATION(S)

The present application is a continuation of U.S. patent application Ser. No. 13/827,411, filed Mar. 14, 2013, which claims the benefit of and priority from U.S. Provisional Patent Application Ser. No. 61/617,883, filed Mar. 30, 2012, the disclosures of which are incorporated herein by reference in their entireties.

FIELD

The present technology relates to laboratory liquid handling systems and, more particularly, to lab members for use in laboratory liquid handling systems and laboratory liquid handling systems and methods incorporating the same.

BACKGROUND

Laboratory liquid handling systems are used to transport and operate on volumes of liquid. For example, one or more liquid samples may be provided in containers (e.g., microwell plates or vials) in a liquid handling system. The liquid handling system may include one or more pipettors that are used to remove (e.g., by aspirating) portions of the samples from the containers and/or to add (e.g., by dispensing) material to the samples in the containers. In some cases, it may be desirable or necessary to move labware or tools within the system. For example, it may be desired to place a lid on a container, to remove a lid from a container, or to move a container (e.g., to a heating station, agitator or sensor). It may be desirable or necessary to execute the aforedescribed procedures robotically and, in some cases, automatically and programmatically.

SUMMARY

According to embodiments of the technology, a laboratory liquid handling system includes a pipetting module, a lab member, and a drive system. The pipetting module includes a pipettor. The pipettor includes a pipettor shaft and a pipetting tip extending from an end of the pipettor shaft. The lab member includes a body and at least one adapter structure including an interlock feature configured to laterally receive and interlock with the pipettor shaft to releasably secure the lab member to the pipettor shaft. The drive system is operable to: selectively move the pipettor shaft laterally relative to the interlock structure to engage the pipettor shaft with the interlock structure to secure the lab member to the pipetting module; move the pipetting module to transport the lab member secured thereto; and selectively move the pipettor shaft laterally relative to the interlock structure to disengage the pipettor shaft from the interlock structure to thereby release the lab member from the pipetting module.

In some embodiments, the laboratory liquid handling system further includes a cradle adapted to be engaged and transported by the lab member. The cradle is configured to removably support a lab object. According to some embodiments, the lab object includes a liquid container configured to hold a quantity of a liquid, and the lab member includes a lid configured to close the liquid container and removable from the liquid container.

In some embodiments, the pipetting module includes a second pipettor including a second pipettor shaft and a second pipetting tip extending from an end of the second pipettor shaft. The at least one adaptor structure includes a second interlock feature configured to laterally receive and interlock with the second pipettor shaft to releasably secure the lab member to the second pipettor shaft. According to some embodiments, the first interlock structure includes a first substantially U-shaped support flange defining a first flange slot and a first lateral opening in communication with the first flange slot, the second interlock structure includes a second substantially U-shaped support flange defining a second flange slot and a second lateral opening in communication with the second flange slot, and the first and second support flanges are opposingly arranged such that the first and second lateral openings face one another.

According to some embodiments, the laboratory liquid handling system includes a liquid handler fluidly connected to the pipetting tip and operable to dispense and/or aspirate a liquid through the pipetting tip.

According to method embodiments of the technology, a method for transporting a lab member using a laboratory liquid handling system including a pipetting module and a drive system, the pipetting module including a pipettor, the pipettor including a pipettor shaft and a pipetting tip extending from an end of the pipettor shaft, includes providing a lab member including: a body; and at least one adapter structure including an interlock feature configured to laterally receive and interlock with the pipettor shaft to releasably secure the lab member to the pipettor shaft. The method further includes: selectively moving the pipettor shaft laterally relative to the interlock structure to engage the pipettor shaft with the adapter structure to secure the lab member to the pipetting module; moving the pipetting module to transport the lab member secured thereto; and selectively moving the pipettor shaft laterally relative to the interlock structure to disengage the pipettor shaft from the interlock structure to thereby release the lab member from the pipetting module.

In some embodiments, the method further includes: providing a cradle removably supporting a lab object; engaging the cradle with the lab member; and transporting the cradle and the lab object supported thereby using the pipetting module. In some embodiments, the lab object includes a liquid container configured to hold a quantity of a liquid, and the lab member includes a lid configured to close the liquid container and removable from the liquid container.

According to some embodiments, the pipetting module includes a second pipettor including a second pipettor shaft and a second pipetting tip extending from an end of the second pipettor shaft, the at least one adaptor structure includes a second interlock feature configured to laterally receive and interlock with the second pipettor shaft to releasably secure the lab member to the second pipettor shaft, and the method includes: selectively moving the second pipettor shaft laterally relative to the second interlock structure to engage the second pipettor shaft with the second interlock structure to secure the lab member to the second pipetting module; and selectively moving the second pipettor shaft laterally relative to the second interlock structure to disengage the second pipettor shaft from the second interlock structure to thereby release the lab member from the second pipetting module. In some embodiments, the first interlock structure includes a first substantially U-shaped support flange defining a first flange slot and a first lateral opening in communication with the first flange slot, the second interlock structure includes a second substantially U-shaped support flange defining a second flange slot and a second lateral opening in communication with the second flange slot, the first and second support flanges are opposingly arranged such that the first and second lateral openings face one another, and the method includes selectively moving the first and second pipettor shafts in opposed lateral directions to insert the first and second pipettor shafts into the first and second flange slots, respectively. The method may include vertically moving the first and second pipettor shafts into position between the first and second flange slots prior to the step of selectively moving the first and second pipettor shafts in opposed lateral directions to insert the first and second pipettor shafts into the first and second flange slots. In some embodiments, the step of vertically moving the first and second pipettor shafts into position between the first and second flange slots requires substantially zero insertion force.

According to some embodiments, the laboratory liquid handling system includes a liquid handler fluidly connected to the pipetting tip, and the method further includes dispensing and/or aspirating a liquid through the pipetting tip.

According to embodiments of the technology, a lab member for use in a laboratory liquid handling system including a pipetting module and a drive system, the pipetting module including a pipettor, the pipettor including a pipettor shaft and a pipetting tip extending from an end of the pipettor shaft, includes a body and at least one adapter structure. The at least one adapter structure includes an interlock feature configured to laterally receive and interlock with the pipettor shaft to releasably secure the lab member to the pipettor shaft.

In some embodiments, the pipetting module includes a second pipettor including a second pipettor shaft and a second pipetting tip extending from an end of the second pipettor shaft, and the at least one adaptor structure includes a second interlock feature configured to laterally receive and interlock with the second pipettor shaft to releasably secure the lab member to the second pipettor shaft. According to some embodiments, the first interlock structure includes a first substantially U-shaped support flange defining a first flange slot and a first lateral opening in communication with the first flange slot, the second interlock structure includes a second substantially U-shaped support flange defining a second flange slot and a second lateral opening in communication with the second flange slot, and the first and second support flanges are opposingly arranged such that the first and second lateral openings face one another.

Further features, advantages and details of the present technology will be appreciated by those of ordinary skill in the art from a reading of the figures and the detailed description of the preferred embodiments that follow, such description being merely illustrative of the present technology.

DESCRIPTION OF EMBODIMENTS OF THE TECHNOLOGY

Figure 1:
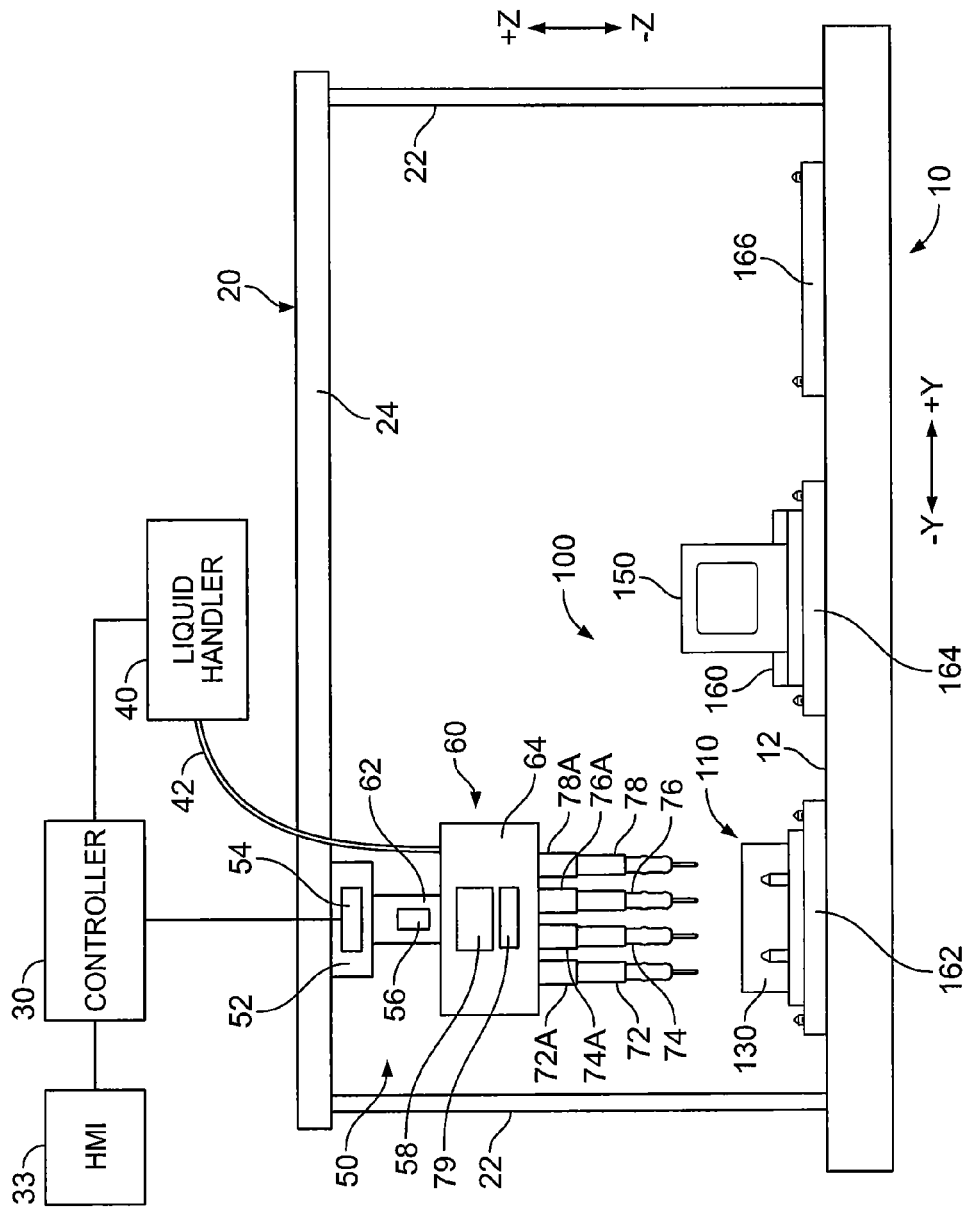
FIG. 1 is a schematic diagram of a laboratory liquid handling system including a lab object handling system according to embodiments of the present technology.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this technology belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

The term "automatically" means that the operation is substantially, and may be entirely, carried out without human or manual input, and can be programmatically directed or carried out.

The term "programmatically" refers to operations directed and/or primarily carried out electronically by computer program modules, code and/or instructions.

The term "electronically" includes both wireless and wired connections between components.

The term "monolithic" means an object that is a single, unitary piece formed or composed of a material without joints or seams.

With reference to FIGS. 1-20, a lab object handling system 100 according to embodiments of the present technology is shown therein. The lab object handling system 100 forms a part of a laboratory liquid handling system 10 (FIG. 1) according to embodiments of the present technology.

With reference to FIG. 1, the system 10 as illustrated includes a platform or deck 12, a frame 20, a controller 30, a human machine interface (HMI) 33, a liquid handler 40, a drive system 50, and a pipetting gantry or module 60. A lab object 160 is disposed on the deck 12. The lab object 160 may include, for example, labware such as a microwell plate, a rack containing one or more vials or another suitable type of liquid container or receptacle. The lab object 160 may be located in a container rack or holder 164. A lifting device rack or holder 162 and a further rack or holder 166 for the lab object 160 may also be provided on the deck 12.

The frame 20 includes supports 22 and one or more conveyor rails 24. The drive system 50 includes a shuttle or carrier 52 operatively mounted on the rail(s) 24 to enable the carrier 52 to move relative to the deck 12. According to some embodiments, the carrier 52 has freedom of movement in at least two lateral degrees (i.e., in an X dimension and a Y dimension). The pipetting module 60 is coupled to and suspended from the carrier 52 by an extension arm 62 such that the pipetting module 60 moves with the carrier 52. The carrier 52 can be driven by a motor or motors 54 under the control of the controller 30. The pipetting module 60 can be further movable in a Z dimension by a motor or motors 56 under the control of the controller 30. A further motor or motors 58 under the control of the controller 30 may be provided to move or reposition further components of the pipetting module 60 as described below.

The liquid handler 40 may be any suitable apparatus that can aspirate and/or dispense a desired amount of a liquid from or into a container. The liquid handler 40 may include, for example, a syringe or pump fluidly connected to the pipetting module 60 by one or more lengths of tubing 42. The liquid handler 40 may be controlled by the controller 30.

With reference to FIG. 1, the pipetting module 60 includes a housing 64 connected to the lower end of the extension arm 62. The pipetting module 60 further includes four pipettors 72, 74, 76 and 78 each coupled to the housing 64 by a respective actuator assembly 72A, 74A, 76A, 78A. An actuator 79 is provided to control the relative positions of the pipettors 72, 74, 76, 78 along the Y axis. As discussed herein, pipetting modules having more or fewer pipettors and actuators may be employed in some embodiments.

Figure 3:
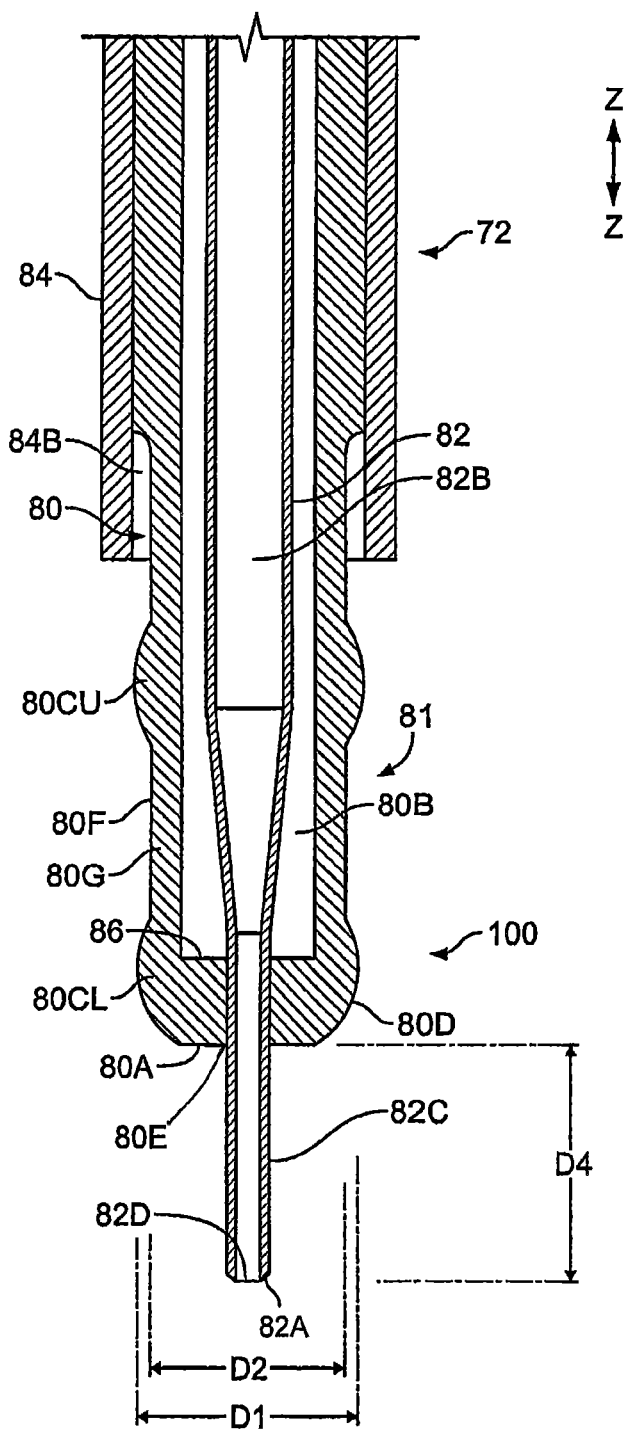
FIG. 3 is a cross-sectional view of a pipettor forming a part of the laboratory liquid handling system of FIG. 1.

A cross-sectional view of the pipettor 72 is shown in FIG. 3 and the pipettors 74, 76, 78 may be constructed in the same manner. Each pipettor 72, 74, 76, 78 includes a pipettor shaft 80, a liquid tube 82, an ejector sleeve 84, and an end wall 86. According to some embodiments, the pipettor shaft 80 is formed of metal.

Referring to FIG. 3, the pipettor shaft 80 defines a passage 80B therethrough that terminates at an opening 80E in a lower terminal end 80A of the pipettor shaft 80. A lower section 80F of the shaft 80 extends beyond the ejector sleeve 84. A pair of axially spaced apart, integral annular ribs 80CU and 80 CL are located on the outer surface of the lower section 80F proximate the lower terminal end 80A. The ribs 80CU, 80CL and a midsection 80G of the lower section 80F define an annular slot or groove 81 therebetween. According to some embodiments, the outer diameter D2 (FIG. 3) of the ribs 80CU, 80CL is in the range of from about 0.017 inch to 0.022 inch greater than the outer diameter D1 of the midsection 80G (i.e., the bottom of the groove 81). The lower terminal end 80A of the shaft 80 may have a generally rounded shoulder 80D. The pipettor shafts 80 of the pipettors 72, 74, 76 and 78 define pipettor axes P1-P1, P2-P2, P3-P3 and P4-P4 (FIG. 8), respectively.

The liquid tube 82 (FIG. 3) extends through the passage 80B such that a probe or tip section 82C thereof extends beyond the lower terminal end 80A a distance D4 to a lower terminal end 82A. The distance D4 can vary and, according to some embodiments, is in the range of from about 0 to 0.63 inch. A passage 82B extends through the liquid tube 82 to provide fluid communication between an end opening 82D and the liquid handler 40 (via the tubing 42). A liquid tight seal can be provided between the liquid tube 82 and the pipettor shaft 80 by the end wall 86.

The ejector sleeve 84 defines a passage 84B and surrounds the pipettor shaft 80. The ejector sleeve 84 is slidable up and down the pipettor shaft 80 under the power of the motor 58 (i.e., along the Z axis).

The actuator assemblies 72A, 74A, 76A and 78A can extend and retract (i.e., lower and raise) the pipettors 72, 74, 76 and 78, respectively, along the Z axis relative to the housing 64 and independently of one another. Additionally, each actuator assembly 72A-78A can slidably extend and retract the ejector sleeve 84 of its associated pipettor 72-78 down and up the length of the pipettor shaft 80 on which the ejector sleeve 84 is mounted.

Figure 8:
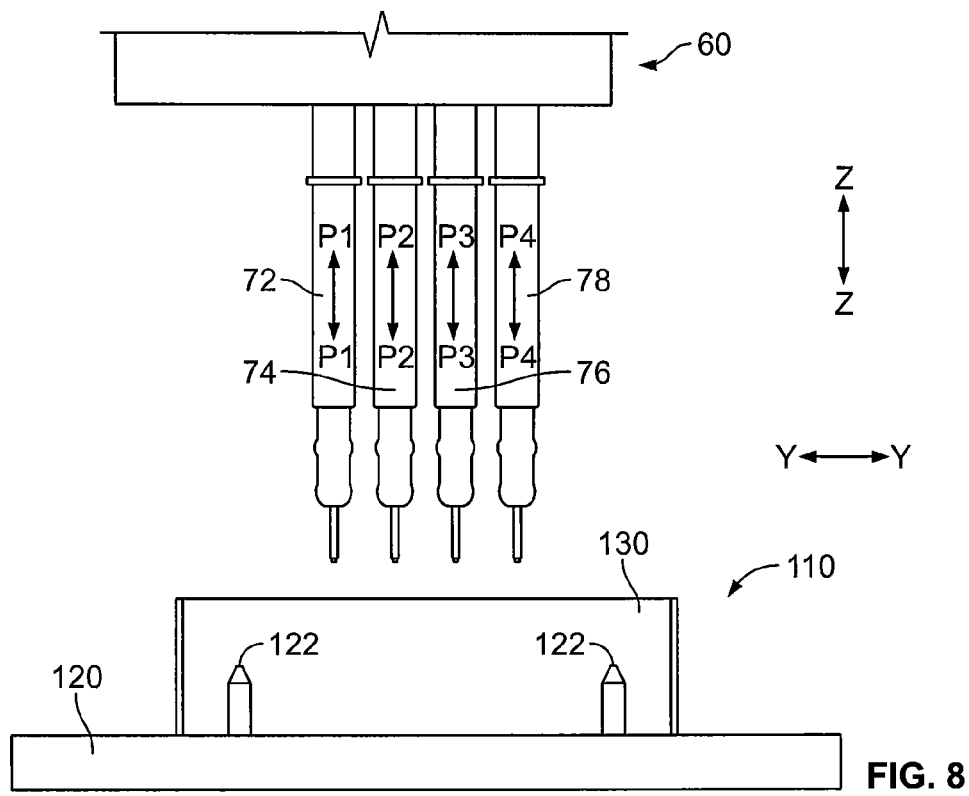
FIG. 8 is an end view of a pipetting module and the lifting device positioned to initiate a procedure for engaging and moving the lifting device in accordance with method embodiments of the present technology.
Figure 9:
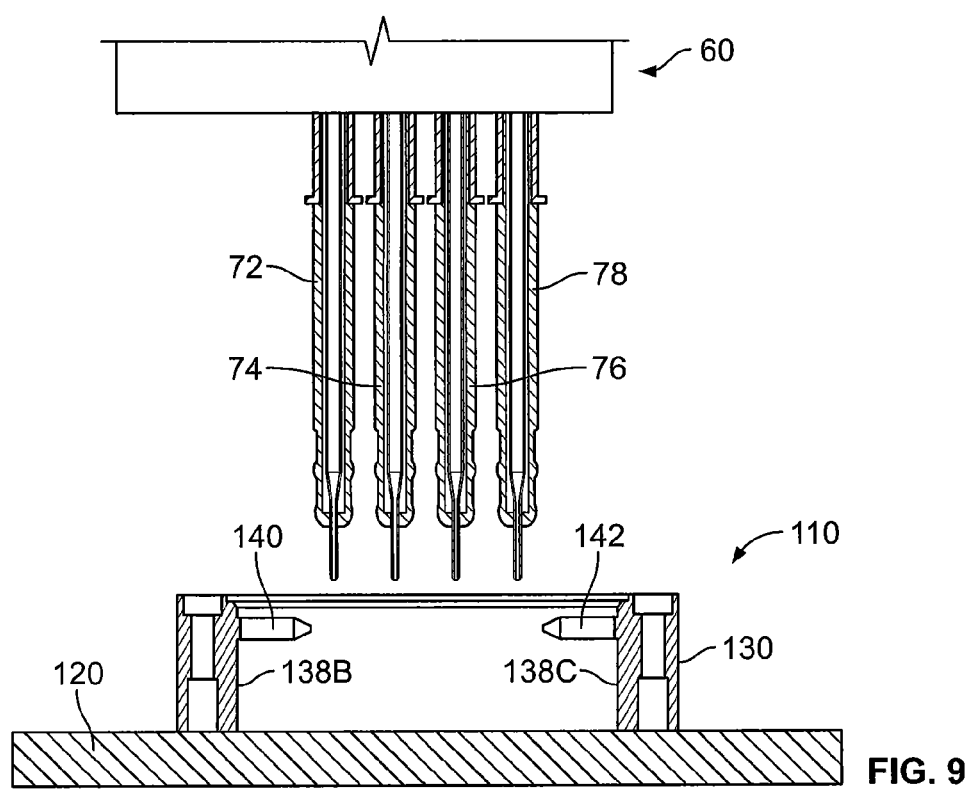
FIGS. 9-12 are fragmentary, center lateral cross-sectional views of the pipetting module and the lifting device illustrating steps of the procedure for engaging and moving the lifting device.
Figure 10:
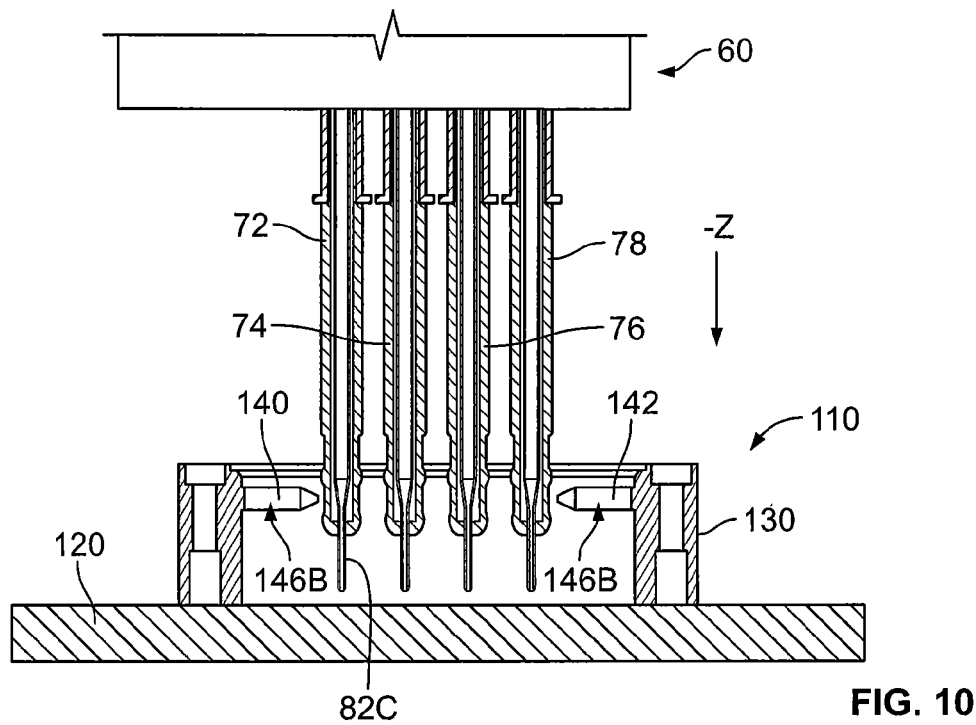
Figure 12:
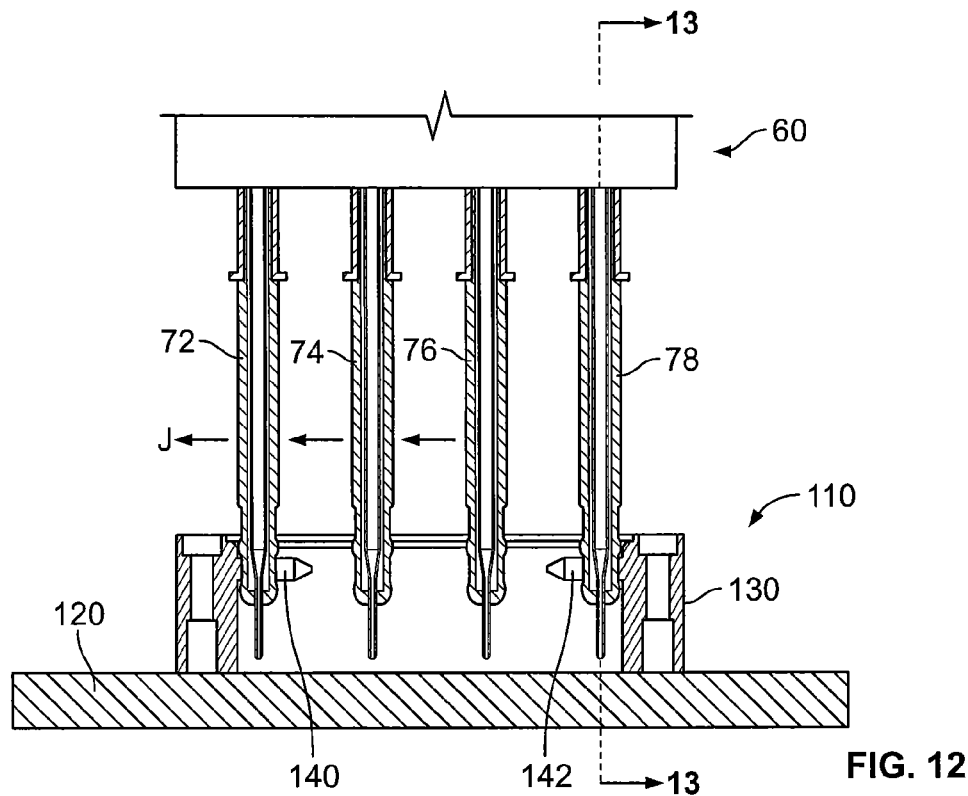

The actuator 79 can be used to selectively spread the pipettors 72-78 apart from one another along the Y axis. More particularly, the pipettors 72-78 can assume a laterally retracted position as shown in FIGS. 8-10 wherein the pipettors 72-78 are positioned in relatively close proximity to one another. The actuator 79 can drive each pipettor 72, 74, 76 laterally (along the Y axis) to the left away from the pipettor to its right so that the pipettors 72-78 assume a laterally extended or expanded position as shown in FIG. 12. In the illustrated embodiment, the pipettor 78 is held stationary, relative to the carrier housing 60. However, other arrangements may be used such as expanding all of the pipettors 72-78 from the center or holding the opposite pipettor 72 stationary while laterally moving the other pipettors 74, 76, 78 apart along the Y axis.

Figure 4:
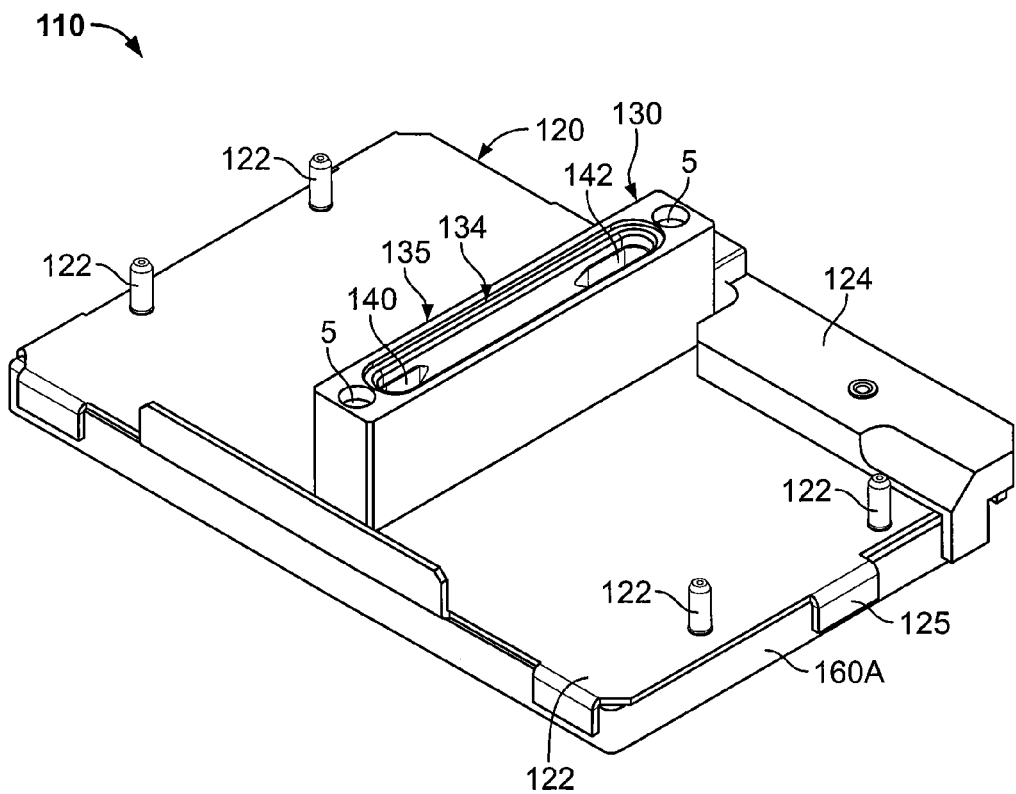
FIG. 4 is a top perspective view of a lifting device forming a part of the lab object handling system of FIG. 1.
Figure 5:
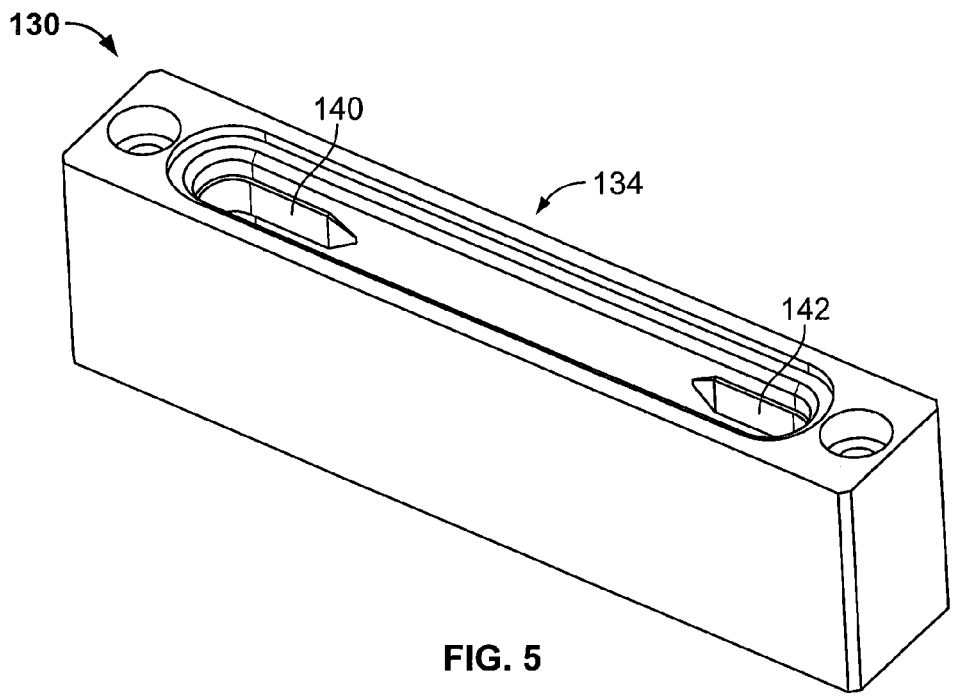
FIG. 5 is a top perspective view of an adapter structure forming a part of the lifting device of FIG. 4.
Figure 6:
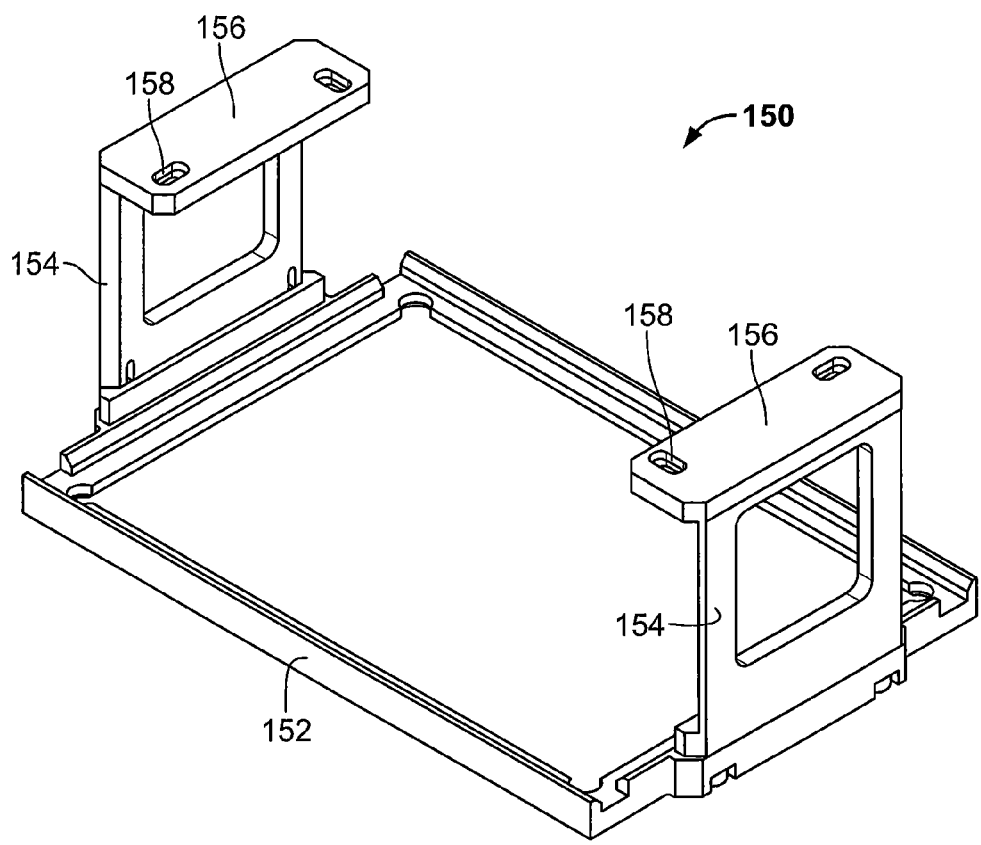
FIG. 6 is a top perspective view of a cradle forming a part of the lab object handling system of FIG. 1.

The lab object handling system 100 includes a lab member in the form of a primary carrier or lifting device 110 (hereinafter, the lifting device 110; FIG. 4) and a frame, secondary carrier, secondary adapter or cradle 150 (hereinafter, the cradle 150; FIG. 6). The lifting device 110 and the cradle 150 can be combined to form a carrier assembly 105 (FIG. 17), as discussed below.

The lifting device 110 (FIG. 4) includes a carrier body 120, a set of stabilizer posts 122 extending upwardly from the carrier body 120, and an adapter structure 130 mounted on top of the carrier body 120. The adapter structure 130 may be affixed to the body 120 by any suitable technique, such as fasteners 5, adhesive, welding, or unitary molding or machining.

According to some embodiments and as shown, the lifting device 110 is a lid assembly and the carrier body 120 includes a frame 125 adapted to releasably hold and retain a lid 160A configured to cover the plate 160. A latch mechanism 124 (e.g., spring-actuated) may be provided to retain the lid 160A.

The adapter structure 130 (FIGS. 4, 5, 9 and 14) includes an elongate main slot 134 communicating with an elongate top opening 135. The slot 134 and the opening 135 are elongated along the Y axis. The slot 134 is defined by opposed side walls 138A (FIG. 13) and opposed end walls 138B and 138C (FIG. 9). The slot 134 defines a slot axis C-C.

A support flange 140 (herein referred to as the left support flange) and a support flange 142 (herein referred to as the right support flange) are provided on the ends 134A and 134B, respectively, of the slot 134 and extend laterally inwardly into the slot 134 from the walls 138A, 138B, 138C. Each support flange 140, 142 is generally U-shaped and defines a flange slot 146B and a sideward or lateral opening 146A communicating with the slot 146B. Each support flange 140, 142 has an end section 148A and opposed side sections 148B. The terminal ends 144 of the flanges 140, 142 may be tapered to assist ingress into the slots 146B. The lateral openings 146A of the support flanges 140, 142 are arranged in an opposed, facing relationship along the slot axis C-C. Each flange slot 146B defines an insertion axis D-D, E-E parallel to the axis C-C.

According to some embodiments, the height H (FIG. 14) of each support flange 140, 142 is in the range of from about 0.019 inch to 0.029 inch.

The adapter structure 130 may be formed of any suitable material(s) such as a moldable or machinable polymeric material. In some embodiments, the adapter structure 130 is formed of polyether ether ketone (PEEK). The adapter structure 130 may be formed using any suitable techniques, such as injection molding.

The cradle 150 includes a base 152, a pair of inwardly extending support flanges 156, and a pair of uprights 154 connecting the support flanges 156 to the base 152. The base 152 as illustrated defines an opening and is configured to cradle and support the plate 160. Stabilizer slots 158 are defined in the support flanges 156.

Figure 2:
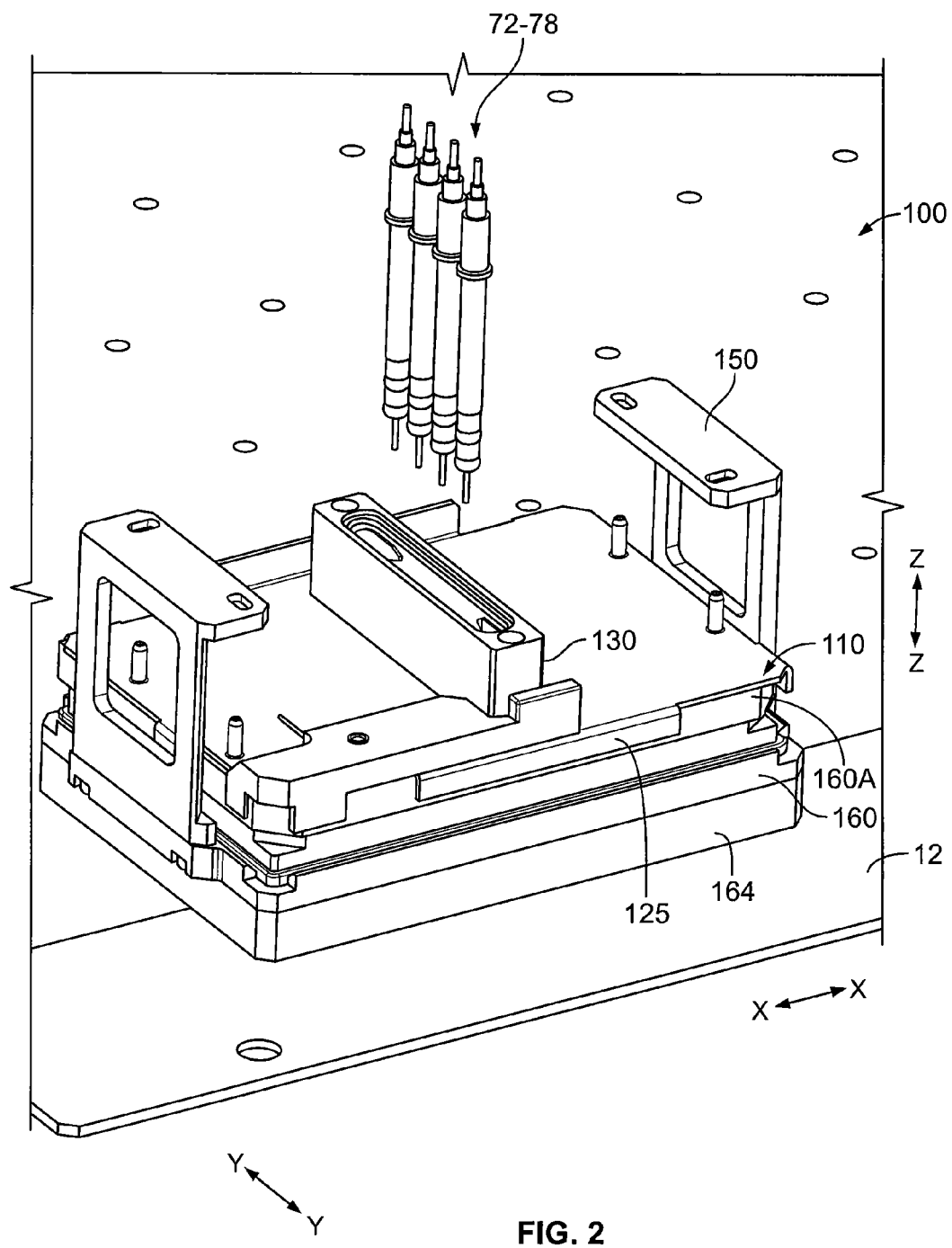
FIG. 2 is a fragmentary, perspective view of the laboratory liquid handling system of FIG. 1.

Exemplary operation of the system 10 and use of the lab object handling system 100 in accordance with methods of the present technology will now be described with reference to FIGS. 8-19. Initially, the lifting device 110 may be seated in the holder 162 (as shown in FIG. 1) and the lab object 160 may be seated in the holder 164 on the deck 12 (as shown in FIGS. 1 and 2). The lab object 160 may be seated in the base 152 of the cradle 150. The lab object 160 may be a microwell plate containing one or more liquid samples, for example. When it is desired to move the lab object 160, the pipetting module 60 and the system 100 can be used as follows. According to some embodiments, the following procedure is executed via or by the controller 30, which controls actuation of the drive motors 54, 56, 58.

The pipetting module 60 is repositioned on the frame 20 and with respect to the deck as needed to align the pipettor axes P1-P1, P2-P2, P3-P3 and P4-P4 with the slot 134, as shown in FIGS. 8 and 9. If needed, the controller 30 may adjust the height of the pipetting module 60 (e.g., lower the pipetting module 60).

With the pipettors 72-78 in the laterally retracted position, the controller 30 then drives the pipettors 72, 74, 76, 78 down (i.e., in the direction −Z) along the axes P1-P1, P2-P2, P3-P3, and P4-P4 such that the pipettor shafts 80 thereof are inserted into the slot 134 as shown in FIG. 10. The pipettors 72, 74, 76, 78 can be driven in this manner by (under the control of the controller 30) driving the housing 64 down with respect to the deck 12 (as shown) and/or by extending the individual pipettors 72, 74, 76, 78 downwardly with respect to the housing 64 using the actuator assemblies 72A, 74A, 76A, 78A.

Figure 11:
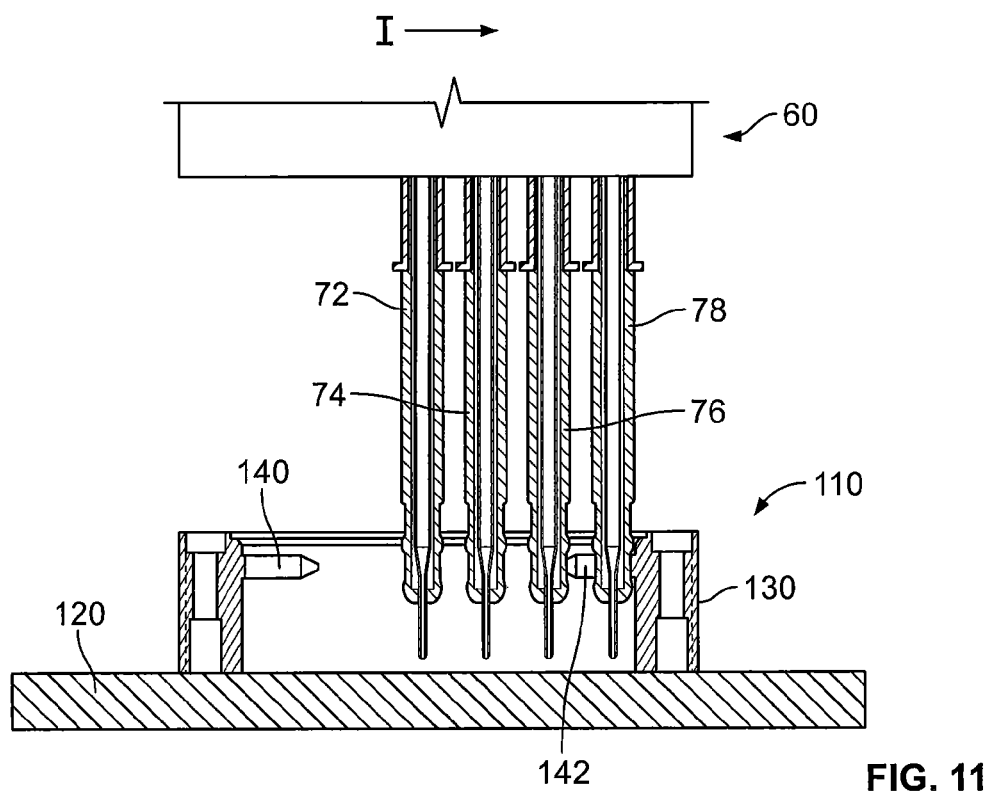

The controller 30 then moves the pipetting module 60 (and thereby the pipettors 72-78 as a group) along the Y axis in a lateral insertion direction I (along the axis D-D) to the position as shown in FIG. 11. In this manner, the pipettor 78 is slid laterally into the flange slot 146B of the support flange 142. In this position, the support flange 142 is axially captured in the pipettor groove 81 of the pipettor 78 between the annular ribs 80CL, 80CU.

The controller 30 then actuates the module 60 to move the pipettors 72, 74, 76 into the laterally expanded position as shown in FIG. 12. In doing so, the pipettor 72 is slid laterally to the left in a lateral direction J (along the axis E-E) into the flange slot 146B of the support flange 140. The flange 140 is thereby likewise axially captured in the pipettor groove 81 of the pipettor 72.

Figure 13:
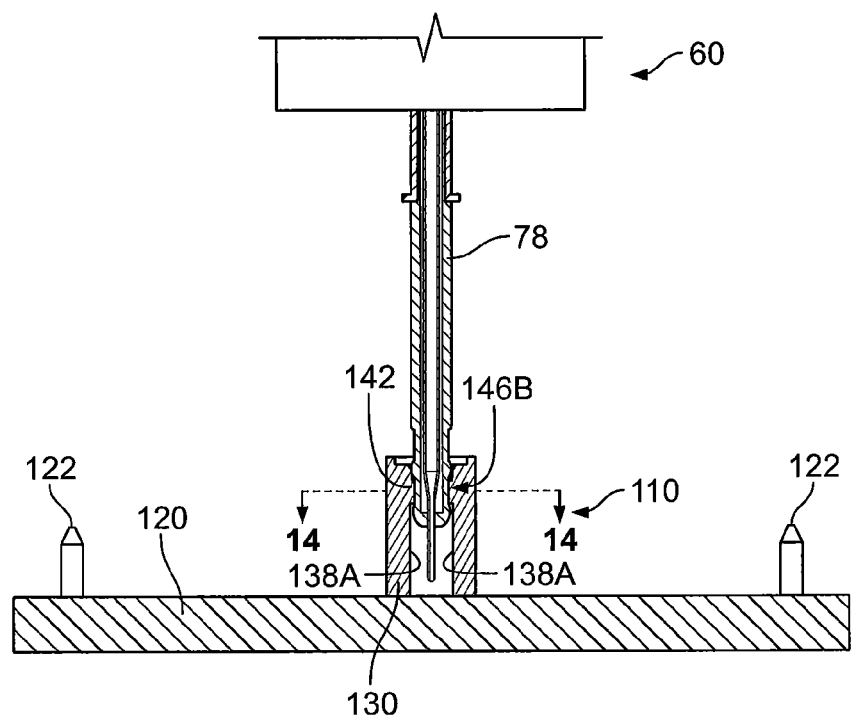
FIG. 13 is a fragmentary, cross-sectional view of the pipetting module and lifting device of FIG. 12 taken along the line 13-13 of FIG. 12.
Figure 14:
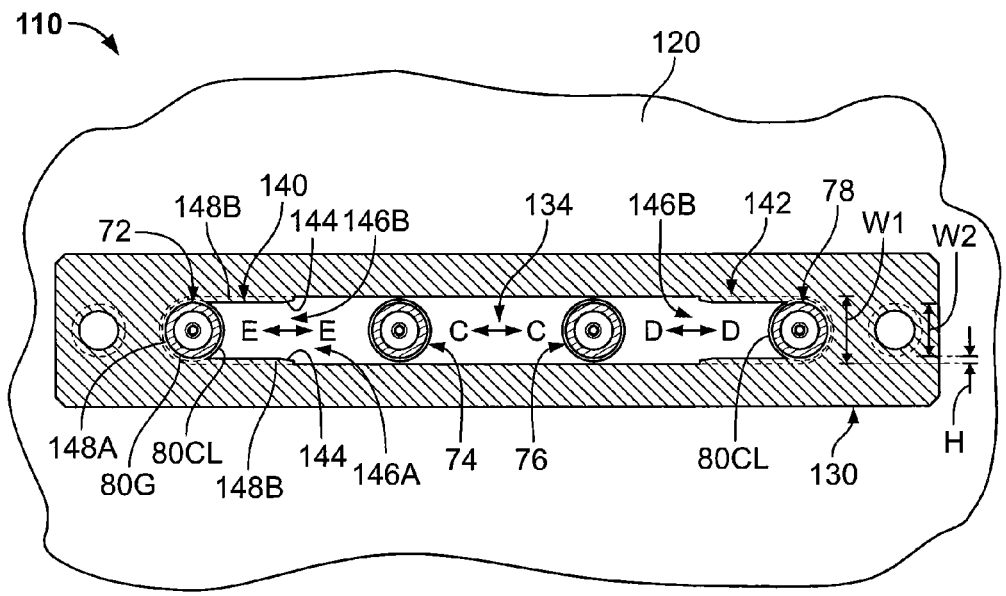
FIG. 14 is a cross-sectional view of the pipetting module and lifting device of FIG. 12 taken along the line 14-14 of FIG. 13.

With reference to FIGS. 12-14, it will be appreciated that the pipettors 72 and 78 are now prevented from being vertically or axially (i.e., along the Z axis) withdrawn from the flange slots 146B by the mechanical interlock between the support flanges 140, 142 and their annular ribs 80CL. That is, the support flanges 140, 142 and the annular ribs 80CL serve as cooperating interlock structures. The pipettors 72 and 78 are also prevented from being laterally withdrawn from the slots 146B by fixed, expanded width or spacing between the pipettors 72 and 78.

Figure 15:
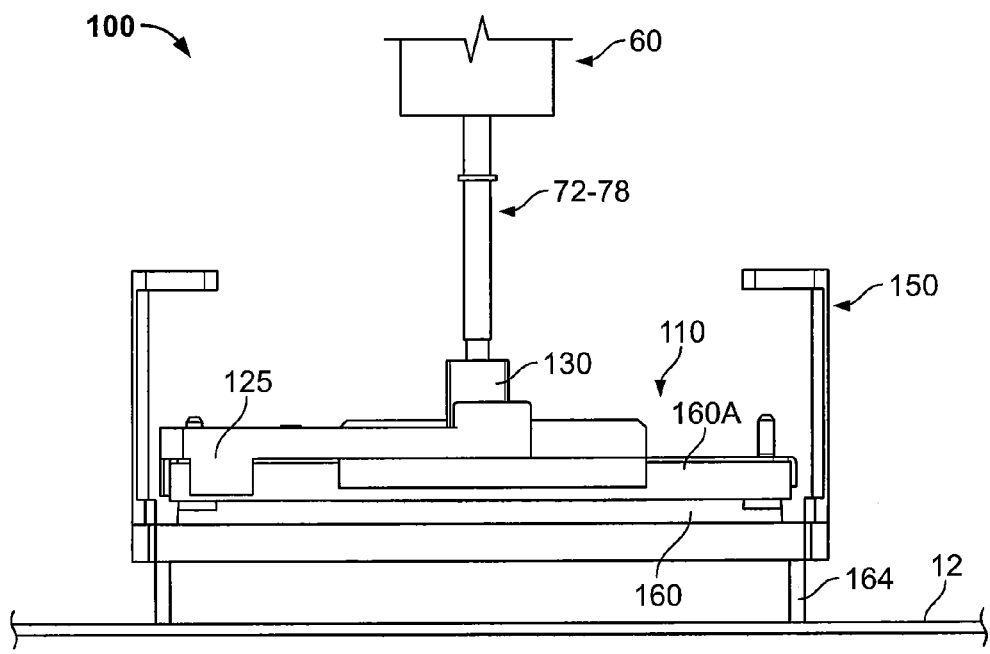
FIGS. 15-19 illustrate steps of a procedure according to method embodiments of the technology for moving a lab object.
Figure 16:
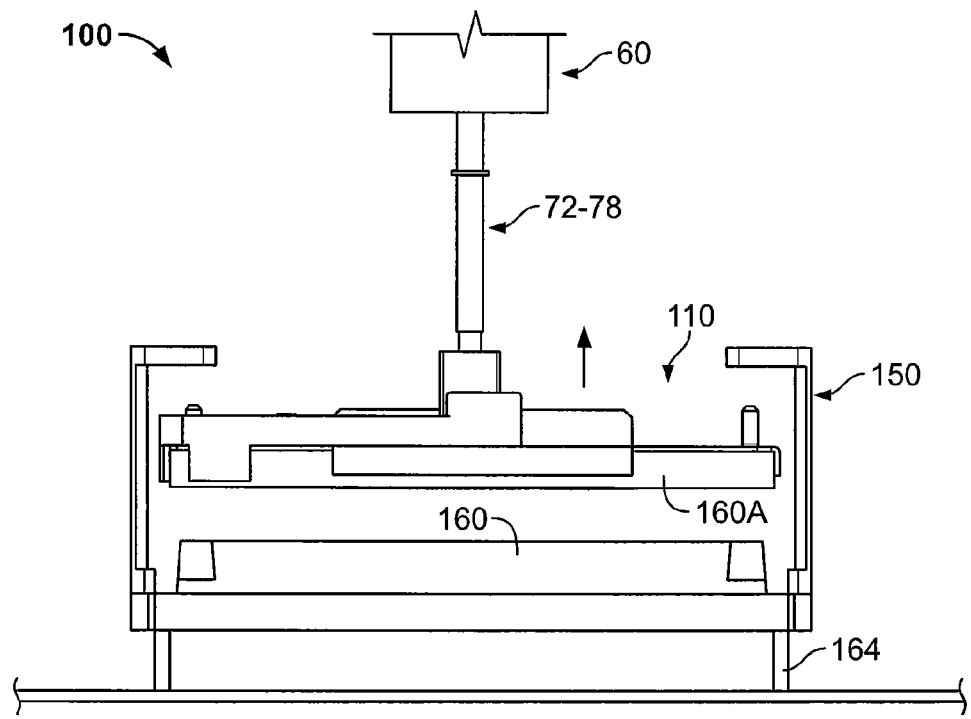
Figure 17:
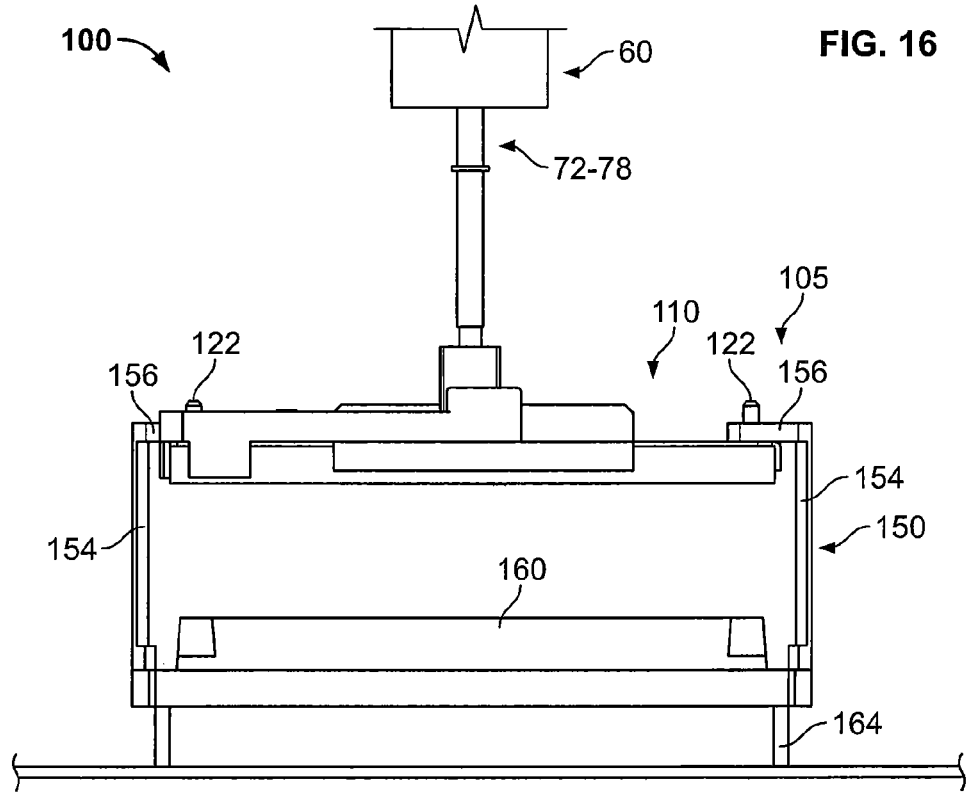

With the lifting device 110 now securely mounted on the pipetting module 60, the controller 30 can lift and transport the lifting device 110 using the module 60. The lifting device 110 is laterally inserted between the uprights 154 as shown in FIG. 15, then raised to engage the body 120 with the support flanges 156 and the stabilizer posts 122 with the stabilizer slots 158 to form the carrier assembly 105 as shown in FIGS. 16 and 17.

Figure 18:
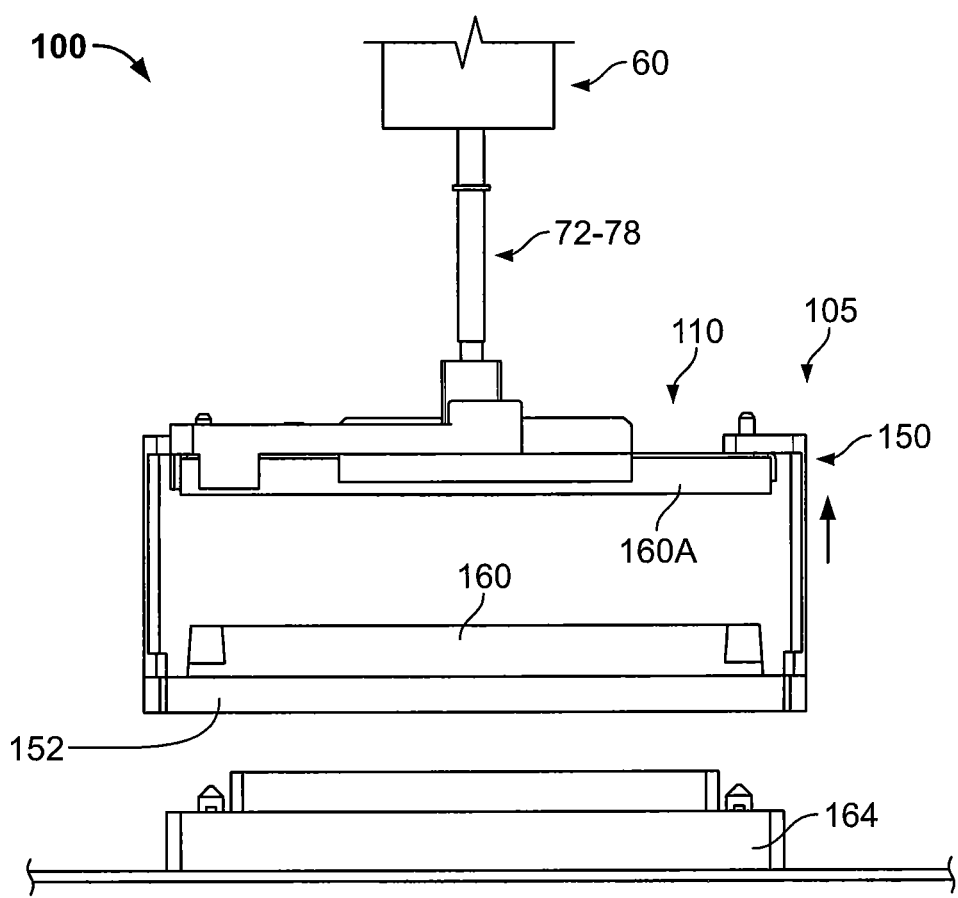
Figure 19:
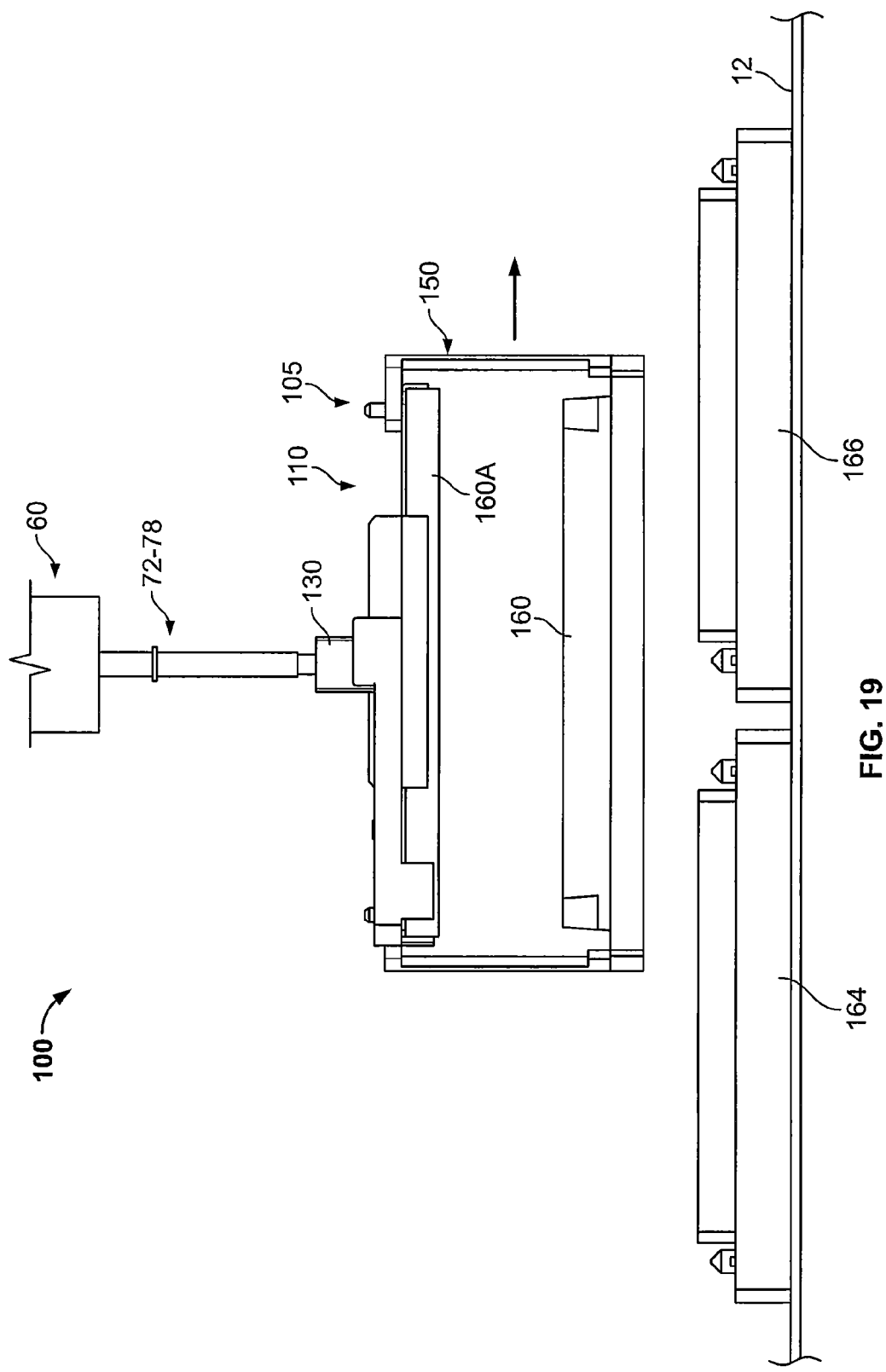

The carrier assembly 105 may thereafter be used to lift and transport the plate 160 using the module 60 under the direction of the controller 30, as shown in FIGS. 18 and 19. By way of example, the carrier assembly 105 can be used to transport the plate 160 from the holder 164 to the tray 166 and deposit the plate 160 in the tray 166.

Figure 7:
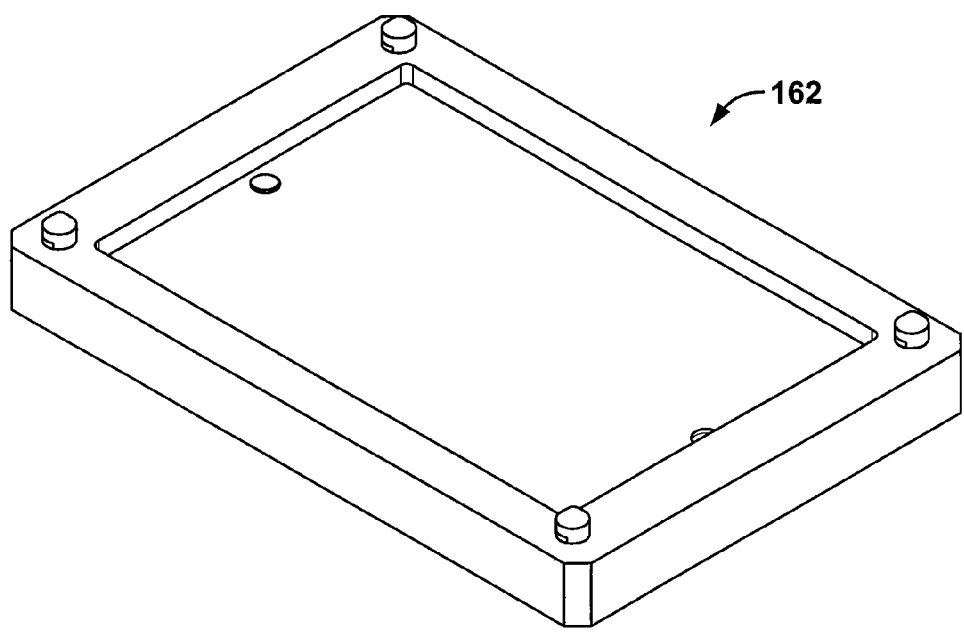
FIG. 7 is a top perspective view of a lifting device holder forming a part of the laboratory liquid handling system of FIG. 1.

The lifting device 110 can then be removed from the cradle 150 by reversing the foregoing steps, leaving the cradle 150 and the plate 160 behind. The pipetting module 60 can be disengaged from the adapter structure 130 by reversing the foregoing steps (that is, by laterally retracting the pipettors 72-78 from the slots 146B and then raising the pipettors 72-78 from the slot 134). The module 60 may be disengaged from the adapter structure 130 while the lifting device 110 is on the plate 160 (in order to keep the lid 160A on the plate 160, if desired) or after the lifting device 110 has been relocated away from the plate 160. The lifting device 110 may be parked for later re-use. FIG. 7 shows an exemplary parking holder 162 for the lifting device 110.

The holder 166 may be of any suitable design or functionality. According to some embodiments, the holder 166 includes a heater, mixer, chiller, or magnetic separation unit.

The main slot 134 has a width W1 (FIG. 14) that is greater than the outer diameters D1 (FIG. 3) of the pipettor annular ribs 80CL, 80CU. Each flange slot 146B has a width W2 (FIG. 14) that is less than the diameter D1 of at least the upper annular rib 80CU and that is greater than the diameter D2 (FIG. 3) of the midsection 80G between the annular ribs 80CL, 80CU.

The lab liquid handling systems and lab object handling systems as disclosed herein can provide a number of advantages. The lab object handling system requires zero insertion force for the pipettors 72-78 entering the adapter structure 130. Only standard (robotic) movements of the pipettors (pipette mandrels) are required to engage with the adapter structure or block 130.

The adapter structure can be compliant in its operation, and tolerant to inconsistencies in machine calibration and labware dimensional tolerances.

The adaptor structure 130 is completely passive. The adapter structure 130 requires no additional latching features, springs, O-rings, or other such hardware in order to attach to the block and any labware moving device the adapter structure 130 may be attached to.

The adapter structure 130 can be designed to lift relatively heavy objects, on the order of several pounds, within the capabilities of the pipetting module drive mechanism.

The adaptor structure 130 can be applied to many different device handlers such that different devices or items could be moved around or on and off the deck of the pipetting workstation without the need of secondary robotic gripping mechanisms.

The procedure as described above can be repeated for re-placement of the lab object 160 and/or transport and placement of other members provided with adapter structures as described.

According to some embodiments and as illustrated, the slot insertion axes D-D, E-E (FIG. 14) and the insertion directions I, J are substantially perpendicular to the insertion direction −Z (e.g., horizontal or perpendicular to vertical). However, in some embodiments, the lateral insertion directions may be transverse but not perpendicular to the insertion direction (e.g., −Z) of the pipettors in the slot 134.

While U-shaped support flanges 140, 142 have been shown and described herein, other configurations of interlock structures may be employed in accordance with other embodiments of the technology.

The pipettors 72, 74, 76, 78 can continue to be used for pipetting using the tips 82C thereof when the pipettors 72, 74, 76, 78 are not installed in the adapter structures. Thus, the liquid handling system 10 can otherwise function in known or other desired manner. For example, the controller 30 can place one or more of the tips 82C of the pipettors 72, 74, 76, 78 in or over a volume of a liquid sample (e.g., in a cell or cells of a microwell plate or other container on the deck 12) and the liquid handler 40 can then aspirate and collect liquid from the volume or dispense a material into the volume. If liquid is collected, the controller 30 can thereafter move the pipettor(s) 72, 74, 76, 78 in or over another location (e.g., cells or containers different from those from which the liquid was collected) and dispense the liquid onto or into this new location.

According to some embodiments and as illustrated in the drawings, the adapter structure 130 is configured relative to the associated pipettors (i.e., the pipettors 72, 74, 76, 78) such that the tips 82C of the pipettors do not contact the adapter structure when the pipettors are inserted in the adapter structure.

While a pipetting module 60 having four pipettors has been described above, embodiments of the technology may include or be adapted for use with pipetting modules having any suitable number of pipettors (e.g., eight). Fewer than all of the pipettors of a given pipetting module may be engaged with the lifting device.

Lab members, lifting devices, systems and methods according to embodiments of the technology can enable a pipettor to be used to pick up, move, assemble, disassemble, and/or release solid objects in a programmable method. These capabilities can be provided without the requirement of a separate, dedicated gripper instrument/device. The cost and space requirements associated with such gripper instruments/devices can thereby be avoided. The adapter structures can be configured to permit easily programmable or executable methods for attaching the lab members to the pipettors and releasing the lab members from the pipettors. The system can be scalable or expandable in that the adapter structures can be integrated with any suitable device or apparatus.

As noted above, operations described herein can be executed by or through the controller 30. The motors 54, 56, 58 and other devices of the pipetting module 60 and/or the liquid handler 40 can be electronically controlled. According to some embodiments, the controller 30 programmatically executes some, and in some embodiments all, of the steps described. According to some embodiments, the movement of the pipetting module 60 to pick up, move and release the lab member is fully automatically and programmatically executed by the controller 30.

The controller 30 may be any suitable device for providing the functionality described herein. According to some embodiments, the controller 30 is an appropriately configured microprocessor-based personal computer.

Embodiments of the controller 30 logic may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, controller 30 logic may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Figure 20:
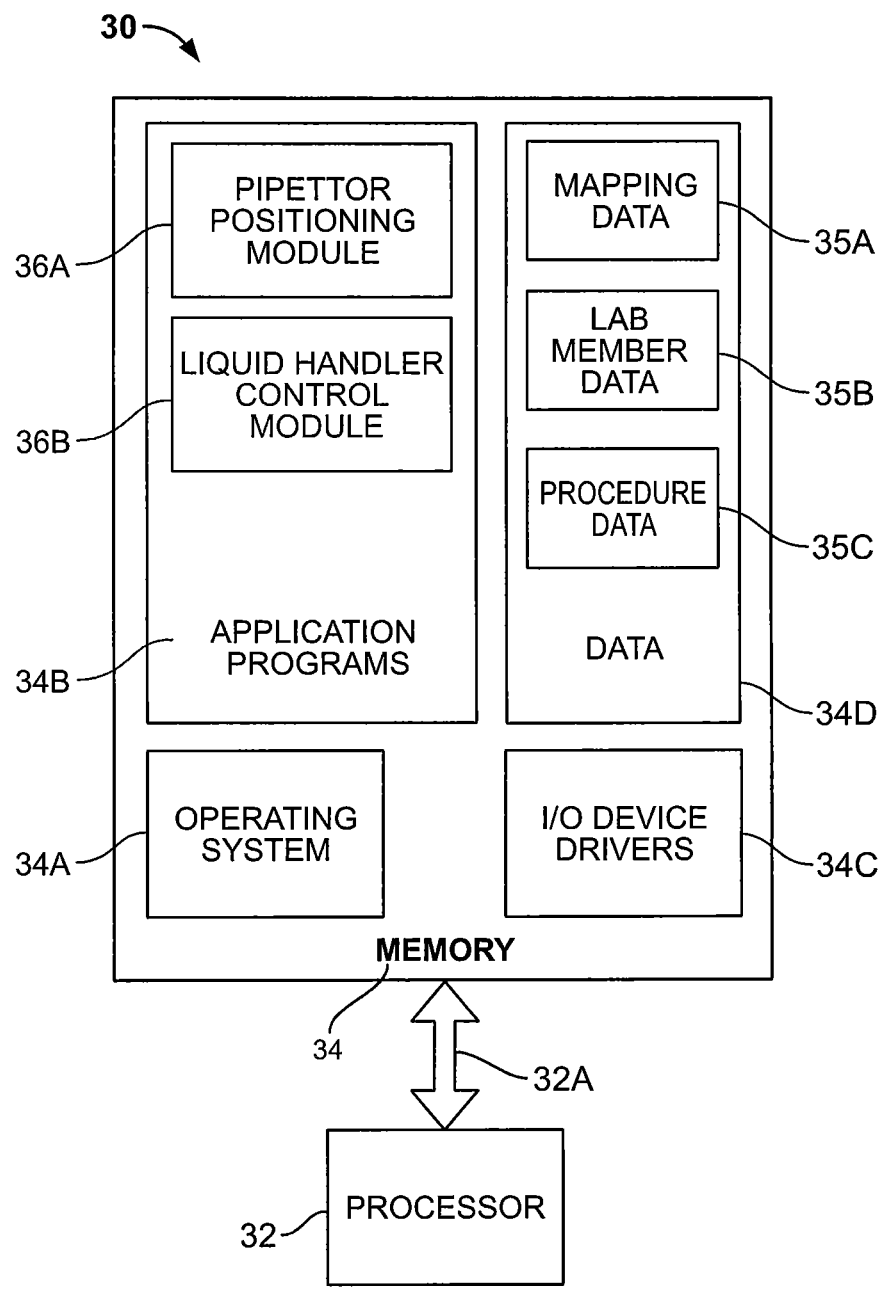
FIG. 20 is a schematic diagram representing a controller forming a part of the laboratory liquid handling system of FIG. 1.

FIG. 20 is a schematic illustration of a circuit or data processing system that can be used in the controller 30. The circuits and/or data processing systems may be incorporated in a digital signal processor 32 in any suitable device or devices. The processor 32 communicates with the HMI 33 and memory 34 via an address/data bus 32A. The processor 32 can be any commercially available or custom microprocessor. The memory 34 is representative of the overall hierarchy of memory devices containing the software and data used to implement the functionality of the data processing system. The memory 34 can include, but is not limited to, the following types of devices: cache, ROM, PROM, EPROM, EEPROM, flash memory, SRAM, and DRAM.

FIG. 20 illustrates that the memory 34 may include several categories of software and data used in the data processing system: the operating system 34A; the application programs 34B; the input/output (I/O) device drivers 34C; and data 34D.

The data 34D can include equipment-specific data. FIG. 20 also illustrates that the data 34D can include mapping data 35A, lab member data 35B, and procedure data 35C. FIG. 20 also illustrates that application programs 35B can include a pipettor positioning module 36A and a liquid handler control module 36B. The mapping data 35A can include data representing the positions (e.g., X, Y and Z coordinates) of objects or components in the work space of the system 10, 11. The lab member data 35B can include data representing characteristics of a lab member or lab members. The procedure data 35C can include data representing a protocol or sequence of steps to execute the procedures described herein. The pipettor positioning module 36A can be used to control the motors 54, 56, 58, and the actuators 72A-78A, and 79, for example, to position and reposition the pipetting module 60, the pipettors 72-78, and the ejector sleeves 84. The liquid handler control module 36B can be used to control actuation of the liquid handler 40 to aspirate and/or dispense fluid.

As will be appreciated by those of skill in the art, the operating system 34A may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 34C typically include software routines accessed through the operating system 34A by the application programs 34B to communicate with devices such as I/O data port(s), data storage and certain memory components. The application programs 34B are illustrative of the programs that implement the various features of the data processing system and can include at least one application, which supports operations according to embodiments of the present technology. Finally, the data 34D represents the static and dynamic data used by the application programs 34B, the operating system 34A, the I/O device drivers 34C, and other software programs that may reside in the memory 34.

As will be appreciated by those of skill in the art, other configurations may also be utilized while still benefiting from the teachings of the present technology. For example, one or more of the modules 36A-B may be incorporated into the operating system, the I/O device drivers or other such logical division of the data processing system. Thus, the present technology should not be construed as limited to the configuration of FIG. 20, which is intended to encompass any configuration capable of carrying out the operations described herein. Further, one or more of the modules can communicate with or be incorporated totally or partially in other components, such as the controller 30.

Example

Lab members having integral adapter structures in accordance with the present technology may be used or incorporated in any suitable laboratory liquid handling system. Suitable systems may include the JANUS™ Automated Workstation with any appropriate pipetting arm such as a Varispan™ Pipetting Arm equipped with VersaTip™ pipettors, for example.

In exemplary embodiments, a lab liquid handling system and a lab object handling system in accordance with aspects of the present technology utilize the pipette tip mounting ends of the JANUS VersaTip™ pipettors (pipetting channels) to pick up and move labware from various positions on the deck of the instrument. The VersaTip™ pipettors enter into a clearance slot in the machined block, and then engage with this block by increasing the spacing between the tips, thus locking the block onto the VersaTip™ pipettors. This block is also attached to a lifting device. Thus, by keeping the VersaTip™ pipettors in their "open span" condition, the lifting device may be moved around the deck of the instrument using instrument operating commands that normally would move the Varispan™ arm. This lifting device can then engage with a cradle that holds an item of labware and move that labware to other positions and devices as required in an operating protocol. The lifting device can be disengaged as required so normal pipetting operations can be carried out. The lifting device can be used as needed within the operating protocol.

The lab object handling system enables the user of a JANUS Automated Workstation (automated liquid pipettor) to transfer labware (e.g., microplates and similar SBS format plates) between different locations on the deck of the workstation without the need of a separate robotic arm or robotic plate handling device.

The lab object handling system allows for a simpler and less complicated automated workstation that is also lower in cost yet still allows for plate and labware movement capability. The device enables the integration of accessory devices (e.g., heaters, chillers, shakers, magnetic separators, or other such devices that must perform actions upon the contents of the plate) into a smaller and more cost effective liquid handling platform.

A lab object handling system according to embodiments of the technology may be used with all Varispan JANUS Automated Workstations and similar pipetting devices using VersaTip™ pipettors (or similar) design. The lab object handling system could also be utilized on a Tecan 4- or 8-tip automated pipetting workstation as the Tecan pipetting mandrel is of the same design (outside geometry) as the PerkinElmer Versatip.

The exemplary lab object handling system may be formed and used as follows.
1. The Adapter Block can be machined from PEEK plastic according to design indicated.
2. Adapter block is attached to lifting frame assembly which moves labware between different locations on the deck of the JANUS.
3. JANUS moves pipette arm and Versatips over the adapter block, its location specified in WinPREP programming
    a. VersaTip™ pipettors are lowered in the Z-axis by the Varispan™ arm into the block to a predetermined position.
    b. VersaTip™ pipettors move forward in the Y direction to place tip 4 in the correct location and engaging the tip with the locking feature of the block.
    c. Varispan™ Arm spreads the VersaTip™ pipettors such that the span between tips is increased thus engaging tip 1 with the locking feature of the adapter block at the end opposite of tip 4.
    d. All four tips are then simultaneously moved together in the Z direction to raise and lower the adapter block and lifting device(s) attached to it.
4. The Varispan™ Arm, by moving in the X and Y directions can move the adapter block and plate handler about the deck of the JANUS.
5. When use of the plate moving hardware is complete the release of the adapter block occurs in a sequence of operations opposite of those in step 3 above.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A laboratory liquid handling system comprising:
a pipetting module including a pipettor, the pipettor including a pipettor shaft and a pipetting tip extending from an end of the pipettor shaft;
a lab member including a body and at least one adapter structure including an interlock feature configured to laterally receive and interlock with the pipettor shaft to releasably secure the lab member to the pipettor shaft; and
a drive system including a controller programmed with instructions to:
selectively move the pipettor shaft laterally relative to the interlock structure to engage the pipettor shaft with the interlock structure to secure the lab member to the pipetting module;
move the pipetting module to transport the lab member secured thereto; and
selectively move the pipettor shaft laterally relative to the interlock structure to disengage the pipettor shaft from the interlock structure to thereby release the lab member from the pipetting module.

2. The laboratory liquid handling system of claim 1 further including a cradle adapted to be engaged and transported by the lab member, wherein the cradle is configured to removably support a lab object.

3. The laboratory liquid handling system of claim 2 wherein:
the lab object includes a liquid container configured to hold a quantity of a liquid; and
the lab member includes a lid configured to close the liquid container and removable from the liquid container.

4. The laboratory liquid handling system of claim 1 wherein:
the pipetting module includes a second pipettor including a second pipettor shaft and a second pipetting tip extending from an end of the second pipettor shaft; and
the at least one adaptor structure includes a second interlock feature configured to laterally receive and interlock with the second pipettor shaft to releasably secure the lab member to the second pipettor shaft.

5. The laboratory liquid handling system of claim 1 including a liquid handler fluidly connected to the pipetting tip and operable to dispense and/or aspirate a liquid through the pipetting tip.

6. The laboratory liquid handling system of claim 1 wherein the drive system includes at least one motor, and the controller is programmed with instructions to cause the at least one motor to:
selectively move the pipettor shaft laterally relative to the interlock structure to engage the pipettor shaft with the interlock structure to secure the lab member to the pipetting module;
move the pipetting module to transport the lab member secured thereto; and
selectively move the pipettor shaft laterally relative to the interlock structure to disengage the pipettor shaft from the interlock structure to thereby release the lab member from the pipetting module.

7. The laboratory liquid handling system of claim 6 wherein the controller is programmed with instructions to automatically and programmatically cause the at least one motor to:
selectively move the pipettor shaft laterally relative to the interlock structure to engage the pipettor shaft with the interlock structure to secure the lab member to the pipetting module;
move the pipetting module to transport the lab member secured thereto; and
selectively move the pipettor shaft laterally relative to the interlock structure to disengage the pipettor shaft from the interlock structure to thereby release the lab member from the pipetting module.

8. The laboratory liquid handling system of claim 1 wherein the pipettor includes a pipettor interlock structure on the pipettor shaft configured to interlock with the interlock feature of the adapter structure to releasably secure the lab member to the pipettor shaft.

9. The laboratory liquid handling system of claim 8 wherein the pipettor interlock structure includes an annular rib.

* * * * *